United States Patent [19]

Anderson et al.

[11] Patent Number: 5,157,126

[45] Date of Patent: Oct. 20, 1992

[54] PREPARATION OF A SOLUTION OF STEARAMIDOPROPYL DIMETHYL PYRROLIDONYL METHYL AMMONIUM CHLORIDE IN A POLYHYDRIC ALCOHOL

[75] Inventors: Lowell R. Anderson, Morristown; Ratan K. Chaudhuri, Butler; Robert B. Login, Oakland, all of N.J.

[73] Assignee: ISP Investments Inc., Wilmington, Del.

[21] Appl. No.: 834,945

[22] Filed: Feb. 14, 1992

[51] Int. Cl.$^5$ ............... C07D 207/12; C07D 211/76
[52] U.S. Cl. ................................ 548/546; 514/844; 548/550; 548/568
[58] Field of Search ........... 548/550, 546, 568; 514/844, 845, 846, 847, 848, 788

[56] References Cited

U.S. PATENT DOCUMENTS

| | | | |
|---|---|---|---|
| 2,945,863 | 7/1960 | Buc et al. | 548/550 |
| 4,122,199 | 10/1978 | Cousse et al. | 548/568 X |
| 4,222,766 | 9/1980 | Martin | 548/568 X |
| 4,360,465 | 11/1982 | Buschmann et al. | 548/568 |
| 4,590,069 | 5/1986 | Deckner et al. | 514/848 X |
| 4,732,990 | 3/1988 | Login et al. | 548/550 |
| 4,885,158 | 12/1989 | Tracy et al. | 548/546 X |
| 5,008,104 | 4/1991 | Chaudhuri et al. | 548/550 X |
| 5,049,680 | 9/1991 | O'Lenick | 548/550 |

FOREIGN PATENT DOCUMENTS 0860655  2/1961  United Kingdom ............... 548/550

*Primary Examiner*—Floyd D. Higel
*Attorney, Agent, or Firm*—Walter Katz; Marilyn J. Maue; Joshua J. Ward

[57] ABSTRACT

A solution of stearamidopropyl dimethyl pyrrolidonyl methyl ammonium chloride in a polyhydric alcohol, suitably at a concentration of about 1–30% by weight, preferably 2–20%, and, optimally, about 5–15%, wherein said polyhydric alcohol is a di-, tri-, or tetra hydric alcohol, preferably glycerol, is prepared by (a) slurrying said compound into excess acetone,
(b) filtering the slurry to provide a filter cake of said compound,
(c) forming a solution of said filter cake in a polyhydric alcohol, and
(d) dropping said solution into an evacuated reaction vessel at a suitable rate to minimize excessive foaming while residual acetone is removed therefrom, the solution remaining under substantial full vacuum until substantially all the solution has been added and substantially of the acetone has been removed.

17 Claims, No Drawings

PREPARATION OF A SOLUTION OF STEARAMIDOPROPYL DIMETHYL PYRROLIDONYL METHYL AMMONIUM CHLORIDE IN A POLYHYDRIC ALCOHOL

BACKGROUND OF THE INVENTION

1. Field of the Invention

This invention relates to solubilization of a quaternary salt in a polyhydric alcohol, and, more particularly, to a solution of stearamidopropyl dimethyl pyrrolidonyl methyl ammonium chloride in a polyhydric alcohol, and to a method of making such solutions.

2. Description of the Prior Art

Surfadone ® QSP (ISP), which is stearamidopropyl dimethyl pyrrolidonyl methyl ammonium chloride, is a solid compound which is useful in cosmetic applications as a surfactant and/or conditioner. However, its use is limited because of the difficulty of formulating such solid into commercial cosmetic compositions.

Accordingly, it is an object of the present invention to provide a solution of this compound in an acceptable solvent at a suitable concentration.

Another object of the invention is to provide a method of making the desired solution of the compound in a solvent.

These and other objects and features of the invention will be made apparent from the following description thereof.

SUMMARY

What is provided herein is a solution of stearamidopropyl dimethyl pyrrolidonyl methyl ammonium chloride in a polyhydric alcohol, suitably at a concentration of about 1-30% by weight, preferably 2-20%, and, optimally, about 5-15%, wherein said polyhydric alcohol is a di-, tri-, or tetra hydric alcohol, preferably glycerol.

The desired solution is made by slurrying said compound into excess acetone, filtering the slurry to provide a filter cake of the compound, forming a solution of the filter cake in a polyhydric alcohol, and dropping the solution into an evacuated reaction vessel to substantially remove residual acetone therefrom. In a preferred form of the invention, the remaining acetone in the solution is less than 0.7%.

A preferred solution comprises about 5-15% of said compound in glycerol.

DETAILED DESCRIPTION OF THE INVENTION

In accordance with the invention, solubilization of Surfadone ® QSP (ISP), stearamidopropyl dimethyl pyrrolidonyl methyl ammonium chloride in a polyhydric alcohol is accomplished by slurrying the compound into excess acetone and filtering the slurry to provide a filter cake of the compound containing about 30-40% acetone. The filter cake then is dissolved in a polyhydric alcohol such as a di-, tri- or tetra- hydric alcohol. e.g. a di-, tri- and tetra- alkylene or polyalkylene alcohol, including such polyhydric alcohols as glycerol, ethylene glycol or propylene glycol, or alkylene derivatives thereof. A preferred polyhydric alcohol is glycerol. Thereafter, the solution is dropped into an evacuated reaction vessel to substantially remove residual acetone therefrom. In this manner, the foam produced is dissipated as the liquid enters the reactor and the foam height is controlled by the rate of addition. The resulting product is always under full vacuum and hence loses acetone more readily.

The solution obtained by this procedure contains less than about 0.7% acetone, and the compound in a concentration of about 1-30%, preferably 2-20%, and, optimally, about 5-15%, by weight of the solution.

EXAMPLE 50 g. of Surfadone ® QSP was slurried into 200 ml of acetone and filtered to remove excess acetone. The resulting filter cake contained about 30-40% acetone. This material was then added to a stirred vessel containing 400 g. of glycerol at 35° C. Dissolution was immediate. The resultant solution was then added to a 1 l. evacuated flask (<1 mm) at a suitable rate to minimize excessive foaming. Pumping was continued for 30 minutes while addition of the solution was complete.

The final solution was a Surfadone ® QSP-glycerol composition at a 1:8 ratio, with quaternary salt of 10.27%, residual acetone of 0.2%, pH (50% aqueous) of 4.15, viscosity (cps-25° C.) of 2320 cps, and % solids (calc.) of 11.1%, as a clear yellow solution.

While the invention has been described with particular reference to certain embodiments thereof, it will be understood that changes and modifications may be made which are within the skill of the art. Accordingly, it is intended to be bound only by the following claims, in which:

What is claimed is:

1. A method of making a solution of a solid compound which is stearamidopropyl dimethyl pyrrolidonyl methyl ammonium chloride in a polyhydric alcohol which comprises:
   (a) slurrying said compound into excess acetone,
   (b) filtering the slurry to provide a filter cake of said compound,
   (c) forming a solution of said filter cake in a polyhydric alcohol, and
   (d) dropping said solution into an evacuated reaction vessel at a suitable rate to minimize excessive foaming while residual acetone is removed therefrom, the solution remaining under substantial full vacuum until substantially all the solution has been added and substantially of the acetone has been removed.

2. A method according to claim 1 wherein said polyhydric alcohol is selected from di-, tri- and tetra hydric alcohols.

3. A method according to claim 2 wherein said polyhydric alcohols are selected from di-, tri- and tetraalkylene and polyalkylene alcohols.

4. A method according to claim 2 wherein said polyhydric alcohol is selected from glycerol, ethylene glycol and propylene glycol.

5. A method according to claim 1 wherein the solution obtained comprises about 1-30% by wt. of said compound.

6. A method according to claim 5 wherein said solution comprises about 2-20% by wt. of said compound.

7. A method according to claim 5 wherein said solution comprises about 5-15% by wt. of said compound.

8. A method according to claim 1 which said filter cake contains about 30-40% acetone.

9. A solution which consists essentially of about 1-30% by wt. of stearamidopropyl dimethyl pyrrolidonyl methyl ammonium chloride in a polyhydric alcohol.

10. A solution according to claim 9 which consists essentially of about 2–20% by wt. of said compound.

11. A solution according to claim 9 which consists essentially of about 5–15% by wt. of said compound.

12. A solution according to claim 9 in which said polyhydric alcohol is selected from di-, tri- and tetra hydric alcohols.

13. A solution according to claim 9 wherein said polyhydric alcohols are selected from di-, tri- and tetra hydric alkylene and polyalkylene alcohols.

14. A solution according to claim 9 wherein said polyhydric alcohol is selected from glycerol, ethylene glycol, propylene glycol, and polyalkylene alcohols.

15. A clear yellow solution according to claim 9 wherein said polyhydric alcohol is glycerol.

16. A solution according to claim 9 which consists essentially of about 5–15% of said compound in glycerol.

17. A solution according to claim 9 having less than about 0.7% residual acetone therein.

* * * * *